United States Patent [19]

Domke et al.

[11] Patent Number: 5,855,869
[45] Date of Patent: Jan. 5, 1999

[54] MICROPARTICULATE ABRASIVES

[75] Inventors: Todd William Domke, Newtown, Pa.; Carolyn Green, Princeton, N.J.; Nano Mardones, Freehold, N.J.; Violet Y. Chen, Guttenberg, N.J.

[73] Assignee: Rhodia Inc., Cranbury, N.J.

[21] Appl. No.: 774,561

[22] Filed: Dec. 31, 1996

[51] Int. Cl.⁶ .............................. A61K 7/16; C01B 15/16; C01B 25/26
[52] U.S. Cl. .............................. 424/49; 424/57; 264/109; 423/307; 423/308; 51/308
[58] Field of Search .......................................... 424/49–58

[56] References Cited

U.S. PATENT DOCUMENTS

| | | | |
|---|---|---|---|
| 3,255,285 | 6/1966 | Chilson | 264/109 |
| 4,081,526 | 3/1978 | Asakawa et al. | |
| 4,707,361 | 11/1987 | Gustafson et al. | 424/154 |
| 4,871,396 | 10/1989 | Tsujita et al. | |
| 5,024,826 | 6/1991 | Lenton | |
| 5,149,521 | 9/1992 | Hirose et al. | |
| 5,206,010 | 4/1993 | Inoue et al. | |

FOREIGN PATENT DOCUMENTS

| | | |
|---|---|---|
| PCT/EP/ 03560 | 3/1996 | European Pat. Off. |
| PCT/EP03698 | 3/1996 | European Pat. Off. |

*Primary Examiner*—Shep K. Rose
*Attorney, Agent, or Firm*—John A. Shedden

[57] ABSTRACT

A microparticulate abrasive composition is comprised of chilsonated granules of a low oil absorption compound selected from the group consisting of sodium tetrapyrophosphate, dicalcium phosphate dihydrate, anhydrous dicalcium phosphate, and mixtures thereof. The abrasive composition is useful as a polishing agent and plaque and tartar removing agent in oral dentifrice compositions such as toothpastes, as well as a soft scrubbing agent for delicate hard surfaces, facial masks, and body soaps.

7 Claims, No Drawings

MICROPARTICULATE ABRASIVES

FIELD OF THE INVENTION

The present invention relates generally to abrasive cleaning compositions for the removal of undesirable deposits on smooth surfaces. In particular, the invention relates to the use of abrasives in toothpaste formulations for the removal of food and beverage stains, tartar and plaque from natural teeth and dental prostheses.

BACKGROUND OF THE INVENTION

Many cleaning compounds have been formulated over the years that have incorporated a solid particulate material as an abrasive to aid in the cleaning process whereas the surfactant and solvent components of cleaners chemically interact with the organic deposits that comprise the undesirable stains, film or "dirty" appearance thereon. Abrasives, through forceful agitation, scrub the surface and physically remove the deposits that are difficult to clean chemically. Once physically broken up, the deposits are more susceptible to chemical breakdown by the surfactants, solvents and detergents.

Abrasives have been used for years in household cleaners, hand soaps, denture cleaners and the like. Pharmaceutically acceptable and food grade compounds have also been used in oral compositions to assist in the breakdown and removal of plaque, tartar, and food stains from teeth. U.S. Pat. No. 4,081,526 to Asakawa et. al. discloses and claims a dentifrice composition with increased polishing power for the removal of plaque and tartar using an abrasive comprised of a combination of an alkali metal phosphate and 0.5 wt % to 13.0 wt % of either monomorillonite or hectorite. The monomorillonite fraction consists of silicon dioxide, magnesium oxide, sodium oxide, iron oxide, and disodium oxide while the hectorite fraction is comprised of a mixture of the same components in different percentages. It is alleged that the combination of the abrasive components produces a synergistic effect, not only in the removal of the plaque and tartar from the surface of the tooth but in the prevention of subsequent plaque deposition.

U.S. Pat. No. 4,871,396 to Tsujita et. al. discloses toothpaste formulations wherein water insoluble binders such as colloidal silica, calcium silicate, montmorrillonite, and magnesium hydroxide, among others, are used to prepare microparticulate granules for use as an abrasive on the surface of the tooth. The granules themselves are comprised of dibasic calcium phosphate, sodium metaphosphate, magnesium carbonate, and mixtures thereof. The granules allegedly serve as excellent polishing abrasives on the tooth surface which results in a pleasant mouth feel.

U.S. Pat. No. 5,149,521 to Hirose et. al. discloses a dentifrice composition comprising a breakable granule consisting of a powder material selected from the group consisting of calcium phosphate, sodium metaphosphate, calcium carbonate, aluminosilicate and the like. The powder material is formed into the granule using a binding agent, resin, fat, polymers, or oils. The breakable granule does so when scrubbed against the tooth during brushing and allegedly imparts a smooth, polished organoleptic feeling in the mouth.

U.S. Pat. No. 5,206,010 to Inoue et. al. also discloses toothpaste formulations comprising abrasive microparticulate granules that consist of a water insoluble powder and a water insoluble organic binder. The water insoluble powder is comprised of sodium metaphosphate, calcium pyrophosphate, magnesium silicate and the like. The binders consist of fat and oils, polymers of methacrylic acid esters, vinyl acetate, PVP, thermoplastic resins and the like. Pharmaceutical agents may also be incorporated for a medicinal therapeutic effect. Again, the granules are processed so as to breakdown during brushing and impart a slippery, smooth mouthfeel.

Published PCT Application No. PCT/EP95/03698 to Vernon et. al. discloses toothpaste compositions containing abrasive agglomerates consisting of silicas, aluminas, calcium carbonate, calcium phosphate, hydroxyapatites and dicalcium phosphate, among others. The agglomerates break down with brushing and are designed to impart a sensorially perceived cleaning benefit without the usually affiliated gritty mouthfeel. The agglomerates are free of binding agents but are comprised of at least two of the enumerated materials, each of which are chemically or physically different from the other.

Published PCT Application No. PCT/EP95/03560 to Stanier et. al. also discloses toothpaste compositions comprising granular abrasives to impart a polished, clean mouthfeel to the teeth. The granules are also comprised of at least two different materials, a high structured water insoluble particulate, (i.e., one with a high oil absorption capacity) such as aluminas and expanded perlites with a low to medium structured water insoluble particulate material (low oil absorption capacity) such as amorphous silicas, calcium carbonate, dicalcium phosphate and the like. The particles also break down in the mouth with the application of shear and aid in the removal of tartar and plaque.

None of the prior art compositions afford a granular microparticulate abrasive comprised of only one material without the need for additional binders and/or agglomerating agents. Nor do any of the prior art materials provide a granule whose particle size is readily controlled and variable depending on the application of use.

SUMMARY OF THE INVENTION

An improved microparticulate granule and method for its preparation consists of sodium tetrapyrophosphate, dicalcium diphosphate dihydrate or anhydrous dicalcium phosphate that is compacted without the use of thickeners and/or organic binding agents. The microparticles range in size from 100 $\mu$–600 $\mu$ and may be incorporated in toothpaste formulations as a polishing abrasive in the removal of tartar, soft scrub hard surface cleaners, facial masks, and chewable tablets.

DETAILED DESCRIPTION OF THE INVENTION

The microparticulate granules of the present invention are prepared from one of two different low structured materials, one water soluble, the other water insoluble. It has been unexpectedly discovered that when compacted using the process of the present invention, a water soluble material such as sodium tetrapyrophosphate can provide excellent abrasive characteristics in toothpastes and other cleaning compositions. It has also been found that a water insoluble material such as dicalcium diphosphate dihydrate, or anhydrous dicalcium phosphate may be similarity compacted using a chilsonator into dense particles or granules which, when incorporated within oral dentifrices such as toothpaste, break apart in the mouth during brushing of the teeth. The degree that the particles fractionate is controlled by the amount of pressure used during the compaction process.

The use of a chilsonator or roll compactor in the method of the present invention also allows for the mediation and control of particle size. The value herein lies in the enablement of toothpaste formulations which comprise large particles (400–600 μm) for a crunchy, more gritty mouth feel and also for the preparation of smaller particles (100–250 μ) for a smoother, more lubricious mouth feel that imparts that "just polished" clean feeling.

Preferably, sodium tetrapyrophosphate, dicalcium diphosphate dihydrate or anhydrous dicalcium diphosphate are compacted to particle sizes falling in a range from about 100 μ to about 600 μ. More preferably, for most toothpaste formulations, the particles will be compacted to a size of from about 200 μ to about 350 μ. The microparticles are incorporated into the toothpaste formulations in an amount of from about 1 to 99% by weight, more preferably in an amount from about 3.0% to about 25% by weight and most preferably in an amount of from about 3.0% to about 10% by weight of the total weight of the toothpaste formulation.

When used in a oral dentifrice formulation as an abrasive material, the composition may be prepared as a toothpaste, cream, gel, or powder. The physical properties of these compositions may be controlled by the delivery vehicle employed and may be varied by adjustment of the solid/liquid ratio and the other components of the system.

The oral compositions of the invention may contain one or more additional components, as will now be described.

Oral compositions of the invention preferably comprise one or more surfactants, preferably selected from anionic, nonionic, amphoteric and zwitterionic surfactants, and mixtures thereof, all being suitable for dental and/or oral use.

Suitable anionic surfactants may include soaps, alkyl sulphates, alkyl ether sulphates, alkylaryl sulphonates, alkanoyl isethionates, alkanoyl taurates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of preferred anionic surfactants may include sodium lauryl sulphate, sodium dodecylbenzene sulphonate, sodium lauroyl sarcosinate and sodium coconut monoglyceride sulphonate.

Nonionic surfactants which may be suitable for use in composition of the invention include sorbitan and polyglycerol esters of fatty acids, as well as ethylene oxide/propylene oxide block copolymers.

Amphoteric surfactants which may be suitable for use in compositions of the invention include betaines such as cocamidopropyl betaine, and sulphobetaines, for example.

The surfactant(s) may be present in the oral composition of the invention in a total amount of from about 0.1 to about 3% by weight.

Anti-caries agents are also preferably employed in the oral dentifrice compositions as is known in the art. Suitable agents include fluoride compounds such as stannous fluoride, sodium fluoride, zinc fluoride and the like. The amounts of these anti-caries agents incorporated in the toothpaste formulations of the present invention are those generally known in the art but will comprise from about 0.01 wt % to about 5.0 wt. % of the total weight of the dentifrice composition and preferably from about 0.05 wt. % to about 2.0 wt. % of the total weight of the composition.

Water is another preferred component of the oral compositions of the invention and may be present in an amount of from about 1 to about 90% by weight, preferably from about 10 to about 60%, and more preferably from about 15 to about 50%.

Toothpastes and creams of this invention may also contain humectants, for example polyols such as glycerol, sorbitol syrup, polyethylene glycol, lactitol, xylitol, and hydrogenated corn syrup. The total amount of humectant, if present, may be, for example, in the range of from about 10 to about 85% by weight of the composition.

In the oral compositions of the present invention it is particularly preferred that one or more thickening agents and/or suspending agents are included, in order to give the composition the desired physical properties (e.g. whether a paste, cream, or liquid) and in order that the chilsonated microparticles remain stably dispersed throughout the composition.

A particularly preferred means for thickening the oral compositions of the invention is by the inclusion of conventional thickening materials such as thickening silicas, examples of which are well known in the art.

Other suitable suspending/thickening agents are well known in the art and include, for example, polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters, esters of ethylene glycol or esters of polyethylene glycol (e.g. fatty acid esters thereof), heteropolysaccharide gums, and cellulose derivatives such as sodium carboxymethyl cellulose.

Particularly suitable thickening agents are heteropolysaccharide gums such as xanthan gum and guar gum.

The thickening agent and/or suspending agent (which may be used singly or as mixtures of two or more such materials) may be present in the composition in a total amount of from about 0.1 to about 50% by weight; preferably from about 5 to about 15% for silica thickening agents; preferably from about 0.1 to about 5% for polymer suspending agents.

The compositions of the invention may contain one or more other components conventionally found in oral compositions. Suitable additional ingredients include: flavoring substances, e.g. peppermint, spearmint; artificial sweeteners; perfume or breath freshening substances; pearlescing agents; peroxy compounds, e.g. hydrogen peroxide or peracetic acid; opacifiers; pigments and colorings; preservatives; moisturizing agents; fluoride-containing compounds; anti-caries agents; anti-plaque agents; therapeutic agents such as zinc citrate, Triclosan (ex Ciba Geigy); proteins; salts; and pH adjusting agents. Furthermore, the compositions usually comprise additional abrasive cleaning agents in amounts of 5–60% by weight, such as abrasive silicas, chalks, hydrated aluminas, calcium phosphate, calcium pyrophosphates, hydroxy apatites, insoluble metaphosphates; etc.

Compositions in accordance with the present invention may be made by conventional methods of preparing oral compositions. Pastes and creams may be prepared using high shear mixing systems under vacuum, for example, with the microparticulate granules which characterize the present invention being added to the pre-mixed base composition in a secondary step comprising dispersing and mixing the microparticulate granules under low shear conditions.

It is generally important in the preparation of compositions in accordance with the invention that any mixing step carried out is done at a sufficiently low shear and/or speed such that the microparticulate granules of the invention do not experience forces sufficiently great to cause the granules to fracture.

The oral compositions of the invention may be used in a similar way to conventional oral compositions such as toothpastes, i.e. a suitable amount of the composition is applied to a brush, or even directly into the mouth, if necessary, with the addition of some water, and the slurry worked on the teeth, gums, and/or other mouth parts as necessary or desired, so as to exert the properties of the microparticulate granules onto the intended intraoral surfaces. Owing to the friability of the granules, any grittiness experienced by the user will soon disappear, so that once the granules have performed their cleaning function, the composition is left free for further polishing or for example, for delivering one or more additional benefits attributable to other components in the composition. Finally, the mouth may be rinsed with water, as with normal oral products. This application's procedure may be repeated as many times as desired.

Whereas a clearly preferred use of the microparticulated granules of the present invention is their incorporation into oral dentifrice compositions such as toothpastes, the granules can also be employed as an abrasive or polishing agent in hand soaps such as Lava®, soft surface scrubbing compositions, chewable tablets, and in facial masks (the various formulations are well known in the art), and the abrasives can be incorporated therein in amounts as deemed necessary according to the type of organic deposit and surface. Cleaners for hard, inert surfaces, for example, will generally use greater proportional amounts of the abrasives than those cleaners for the face and skin.

The following example is provided as a means to teach a specific formulation of an oral dentifrice embodiment of the present invention. The example is for illustrative purposes only, and it is recognized that there are many possible changes that may be made with respect to the ingredients and their respective amounts. It is to be understood that to the extent any such changes do not materially alter the final composition or product, they are to be considered as falling within the spirit and scope of the invention, as later defined by the claims.

Example I

A toothpaste composition with enhanced plaque and tartar control was prepared according to the following formulation:

SILICA MICROGRANULE FORMULATION

| INGREDIENT | WT. % | WT. g |
|---|---|---|
| Distilled Water | 31.350 | 376.20 |
| Sodium Fluoride | 0.243 | 2.92 |
| Trisodium Phosphate Decahydrate | 1.500 | 18.00 |
| Monosodium Phosphate Dihydrate | 0.600 | 7.20 |
| Sodium Saccharin | 0.400 | 4.80 |
| Sorbitol (70% soln.) | 42.807 | 513.68 |
| Xanthan Gum (Rhodicare) | 0.500 | 6.00 |
| Carbopol 980 NF (B. F. Goodrich) | 0.100 | 1.20 |
| Tixosil 103 | 10.000 | 120.00 |
| Microgranular Dicalcium Phosphate Dihydrate | 10.000 | 120.00 |
| Titanium Dioxide | 0.300 | 3.60 |
| FD&C Blue #1 (1% soln.) | 0.100 | 1.20 |
| Sodium Lauryl Sulfate | 1.200 | 14.40 |
| Flavor | 0.900 | 10.80 |
|  | 100.000 | 1,200.00 |

What we claim is:

1. An oral dentifrice composition comprising a microparticulate abrasive consisting of a low oil absorption material chilsonated into granules in the absence of a binding agent dispersed in a pharmaceutically acceptable carrier material.

2. The dentifrice composition of claim 1 wherein said low oil absorption material is dicalcium phosphate dihydrate.

3. The oral dentifrice composition of claim 1 wherein granules range in size of from approximately 100 $\mu$ to about 600 $\mu$.

4. The oral dentifrice of claim 3 wherein said granules range in size of from approximately 200 $\mu$ to about 350 $\mu$.

5. The oral dentifrice of claim 4 further comprising surfactants, anti-caries agents, thickeners, emulsifiers, flavors, sweeteners, solubilizers, fillers, water insoluble polymers and tartar control agents.

6. The oral dentifrice of claim 5 formulated as a toothpaste, gel, cream, mouthwash, or chewable tablet.

7. An oral dentifrice with enhanced plaque and tartar control comprising the microparticulate abrasives of claim 1.

* * * * *